United States Patent
Nabai et al.

[11] Patent Number: 5,388,588
[45] Date of Patent: Feb. 14, 1995

[54] BIOPSY WOUND CLOSURE DEVICE AND METHOD

[76] Inventors: Hossein Nabai, 14555 Levan Rd., Ste. 410, Livonia, Mich. 48154; Homayoon Rahbari, 1314 N. Macomb St., P.O. Box 360, Monroe, Mich. 48161

[21] Appl. No.: 56,399

[22] Filed: May 4, 1993

[51] Int. Cl.⁶ .............................................. A61B 5/00
[52] U.S. Cl. .................................. 128/754; 604/15
[58] Field of Search ............... 128/749, 753, 754; 604/15, 265; 606/108, 167, 170

[56] References Cited

U.S. PATENT DOCUMENTS

| | | |
|---|---|---|
| 363,538 | 5/1887 | Penny . |
| 3,566,871 | 3/1971 | Riall . |
| 4,409,206 | 10/1983 | Stricker .................................. 424/81 |
| 4,605,005 | 8/1986 | Sheehan . |
| 4,744,364 | 5/1988 | Kensey ................................... 604/15 |
| 4,895,559 | 1/1990 | Shippert ................................ 604/15 |
| 5,021,059 | 6/1991 | Kensey et al. ......................... 604/15 |
| 5,080,655 | 1/1992 | Haaga .................................... 128/754 |
| 5,275,616 | 1/1994 | Fowler ................................... 604/15 |

*Primary Examiner*—Max Hindenburg
*Attorney, Agent, or Firm*—Alex Rhodes

[57] ABSTRACT

A method and closure device for performing a routine biopsy procedure without the use of sutures or butterfly bandages. The method and closure device controls bleeding, repairs the biopsy site, reduces the likelihood of inducing excessive scarring and reduces the handling of tissue. The closure device is comprised of a circular sponge made from an absorbable foam material which swells and fills up the defect left by biopsy and an applicator for implanting the sponge into the biopsy site. The sponge is pre-cut to a diameter which approximately corresponds to the diameter of the punch which is used for excising a biopsy specimen. After the specimen is excised the sponge is implanted into the space from which the specimen was taken. A slight pressure is applied to the sponge for approximately 30 to 60 seconds to stop any excess bleeding.

14 Claims, 5 Drawing Sheets

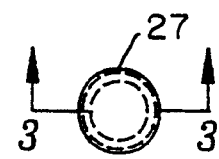
FIG. 1
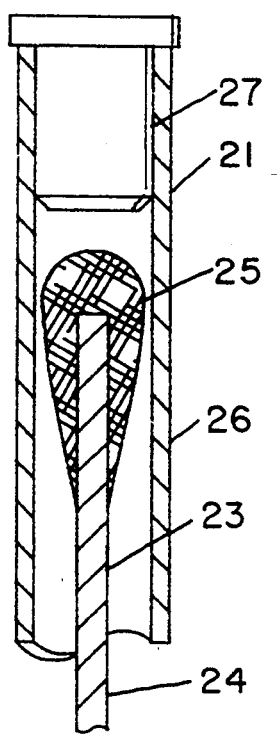
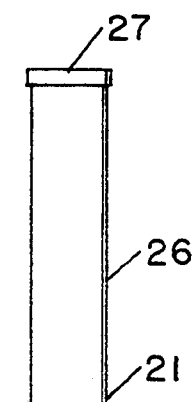
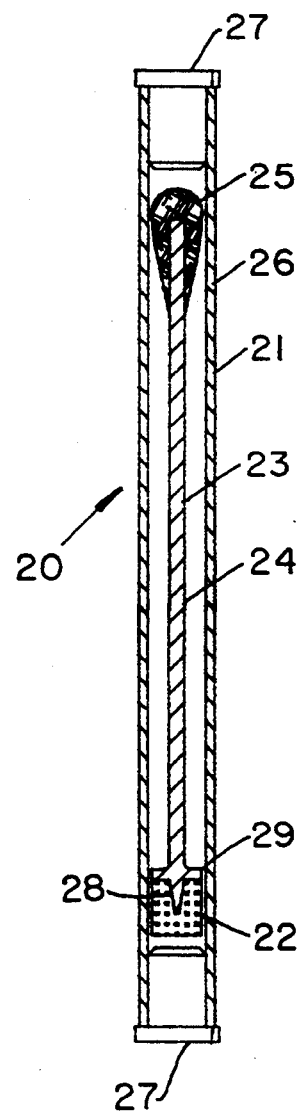
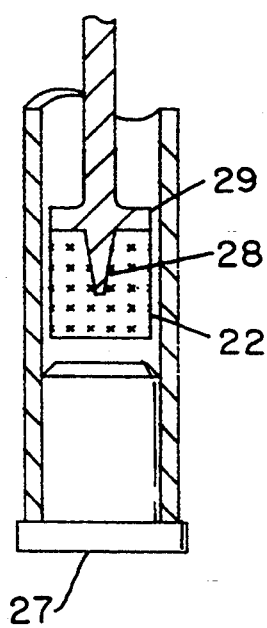
FIG. 4  FIG. 3  FIG. 2

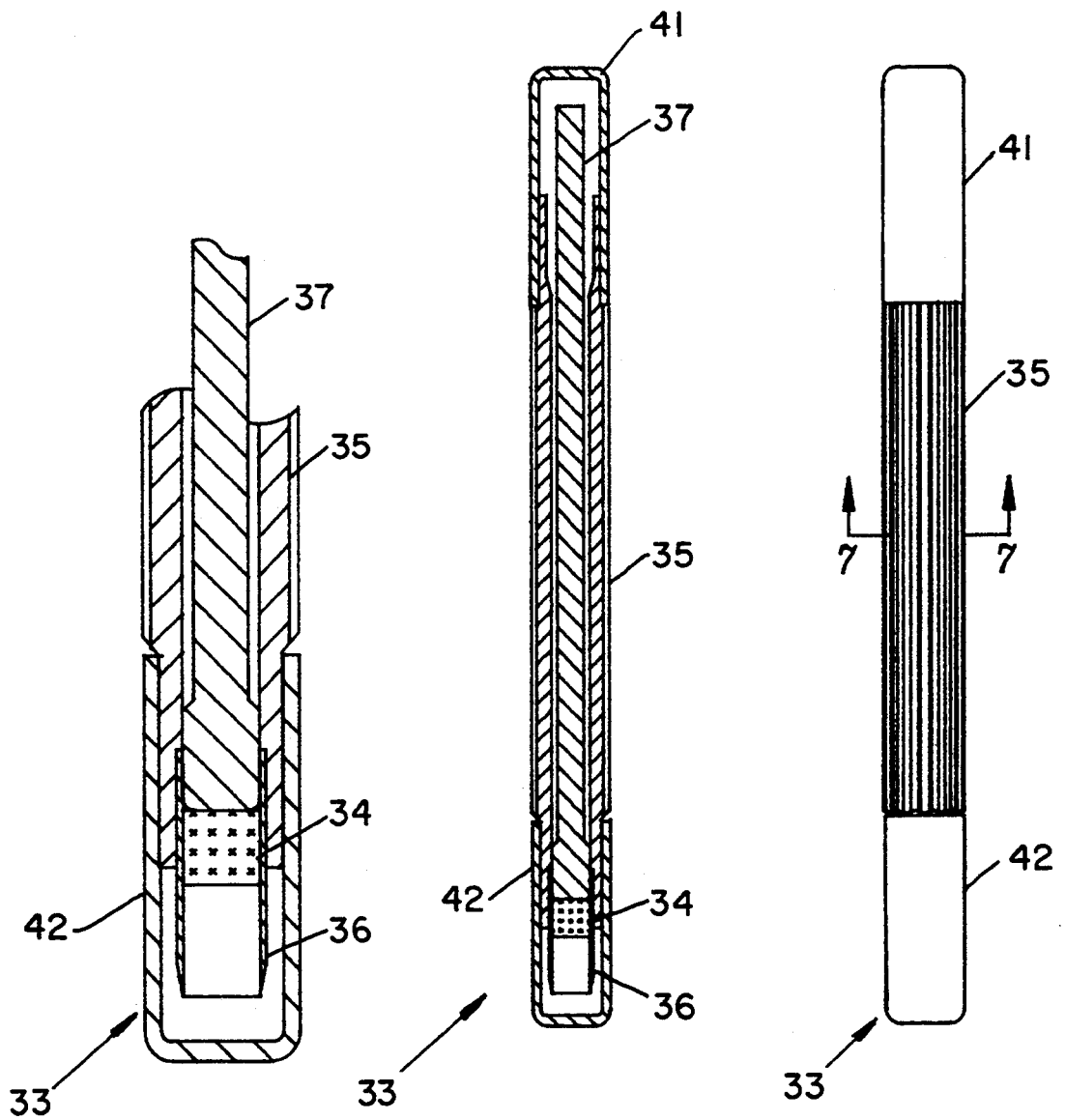

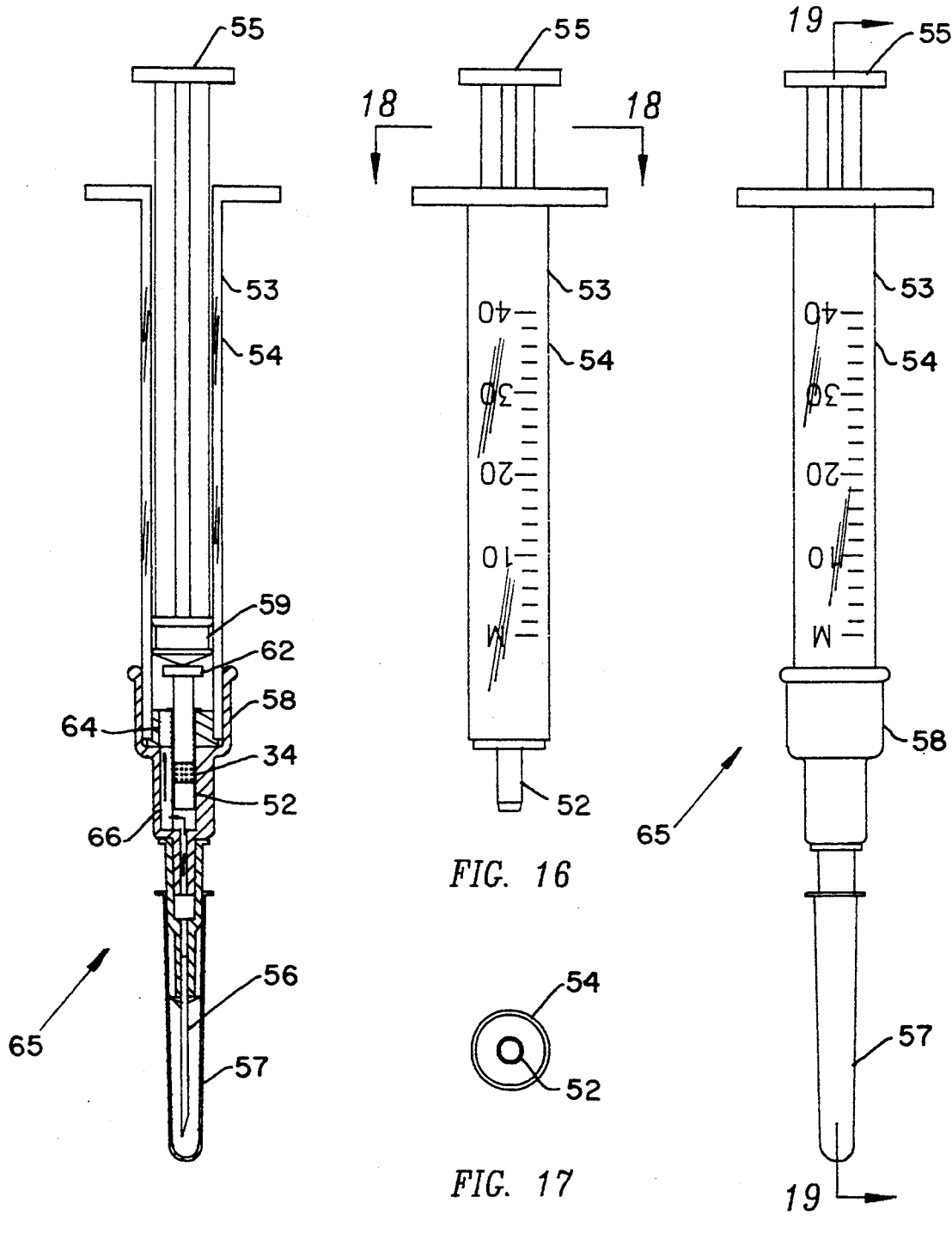

BIOPSY WOUND CLOSURE DEVICE AND METHOD

BACKGROUND OF THE INVENTION

This invention relates to wound closure devices and more particularly to a biopsy wound closure apparatus and method for controlling bleeding and repair of the biopsy site during a routine skin biopsy procedure.

The skin is a complex anatomical system composed of two layers—the epidermis, or epithelium, which is visible to the naked eye, and the dermis or corium, below the epidermis which is firmly interlocked with the dermis. When the skin is punctured, the cells of the surrounding dermis and epidermis multiply to compensate for the loss of cells in the dermis and epidermis. Skin biopsies are frequently performed to diagnose abnormal skin conditions.

Surgical punches, ranging in diameter from 2 to 6 millimeters, are commonly used to excise small samples of skin for medical biopsies. The punches are razor sharp circular knives which are pressed against the skin and rotated to excise cylinder shaped samples for biopsies.

The current practice during a routine skin biopsy procedure is to use sutures, or for small wounds multiple butterfly bandages, to control the flow of blood and to repair the biopsy site. One deficiency with this practice is that some patients suffer anxiety during the suturing of wounds. Another deficiency is that a considerable amount of time is spent by physicians for hemostasis and repair of the biopsy site during routine biopsy procedures.

Sterile sponges have been used as packing material during surgery when hemostatic devices for controlling capillary, venous and arteriolar bleeding are either ineffective or impractical. However, sterile sponges have neither been available nor used to repair biopsy sites or to control bleeding during biopsy procedures. Nor have small pre-cut implant devices having the same or similar diameters as surgical punches been used to repair resulting defects or to control bleeding after excisions of specimens for skin biopsies.

In view of the foregoing, it is apparent that a more efficient, effective, easy to use apparatus and method for performing a routine biopsy procedure would satisy an existing need.

SUMMARY OF THE INVENTION

The present invention satisfies the existing need by providing a pre-cut sterile sponge and applicator for hemostasis and repair of a biopsy site during a routine biopsy procedure.

The invention is comprised of a pre-cut sterile sponge of the approximate shape and size of a specimen which is excised during a skin biopsy procedure and an applicator for inserting the sponge. The closure apparatus and method are effective for controlling bleeding, promoting healing, and reduce the likelihood of excessive scarring.

A further benefit, in the addition to the foregoing benefits, is that damage to the biopsy specimen is reduced because the biopsy procedure is performed with very little manipulation of the tissue.

In the first aspect of the invention, a porous pre-cut sponge is detachably held on one end of a slender applicator. At the other end of the applicator is a sterile wad of cotton fiber. After a biopsy specimen has been excised, the sterile sponge is implanted into the wound with the applicator.

In another aspect of the invention, a pre-cut sterile sponge and applicator are pre-assembled in the hollow interior of a biopsy punch. After a specimen has been excised, the applicator is made accessible by removing a cap from the end of the punch and the sterile sponge is implanted into the wound with the applicator. One advantage of this embodiment is that the sponge can be slightly diametrically pre-compressed to fit more snugly in the wound.

In another aspect of the invention, the sterile sponge and applicator are contained within the interior of a transparent plastic tube. After a specimen has been excised, the sterile sponge is implanted into the wound with the applicator. This embodiment also permits the sponge to be diametrically pre-compressed.

In another aspect of the invention, a pre-cut sterile sponge is combined with a biopsy punch and a syringe.

The foregoing features and benefits of our invention, together with other features and benefits, will be apparent from the ensuing detailed description taken in conjunction with the accompanying drawings. The best mode which is contemplated in practicing our invention is disclosed and the subject matter in which exclusive property rights are claimed is set forth in each of the numbered claims which are appended to the detailed description.

BRIEF DESCRIPTION OF THE DRAWINGS

FIG. 1 is a plan view of a closure device for a routine biopsy procedure which embodies the present invention.

FIG. 2 is a front elevational view of the closure device shown in FIG. 1.

FIG. 3 is a cross-sectional view taken on the line 3—3 in FIG. 1.

FIG. 4 is an enlarged fragmentary view of FIG. 3.

FIG. 5 is a plan view of an alternate embodiment in which a sterile sponge is combined with a biopsy punch.

FIG. 6 is a front elevational view of the alternate embodiment shown in FIG. 5.

FIG. 7 is a cross-sectional view taken on the line 7—7 in FIG. 6.

FIG. 8 is a cross-sectional view taken on the line 8—8 in FIG. 5.

FIG. 9 is an enlarged fragmentary view of FIG. 8.

FIG. 14 is a plan view of an alternate embodiment in which a pre-cut sterile sponge is combined with a biopsy punch and syringe.

FIG. 15 is a front view of the alternate embodiment shown in FIG. 14.

FIG. 16 is a front view of the alternate embodiment shown in FIGS. 14 and 15 with the syringe portion removed.

FIG. 17 is a bottom view of FIG. 16.

FIG. 18 is a cross-sectional view taken on the line 18—18 in FIG. 16.

FIG. 19 is a cross-sectional view taken on the line 19—19 in FIG. 15.

DETAILED DESCRIPTION OF THE PREFERRED EMBODIMENT

Figure 10:
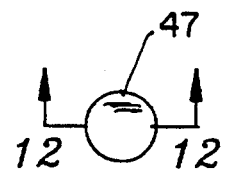
FIG. 10 is a plan view of an alternate embodiment in which a sterile sponge and applicator are stored in a transparent cylindrical tube.
Figure 13:
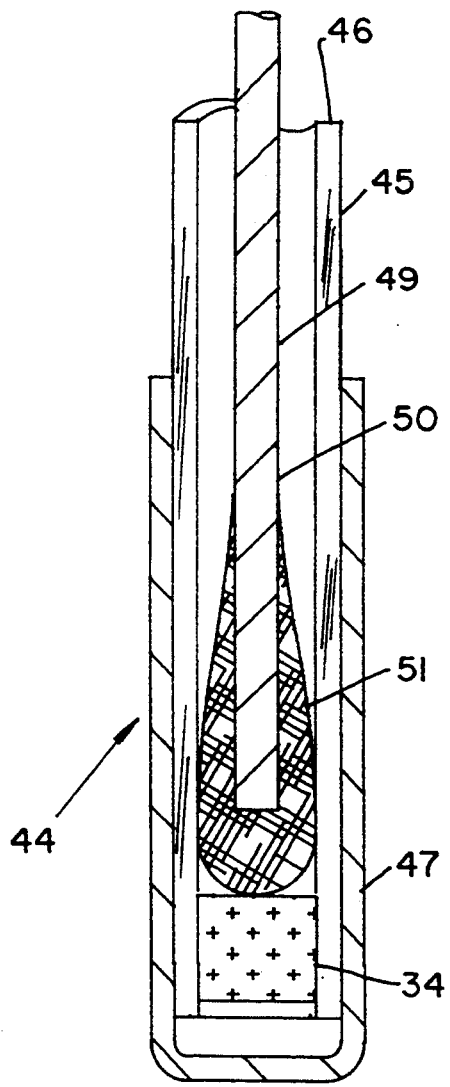
FIG. 13 is an enlarged fragmentary view of FIG. 12.
Figure 12:
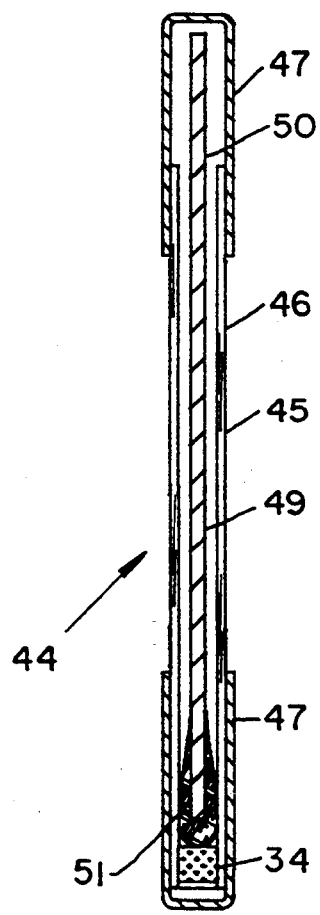
FIG. 12 is a cross-sectional view taken on the line 12—12 in FIG. 10.
Figure 11:
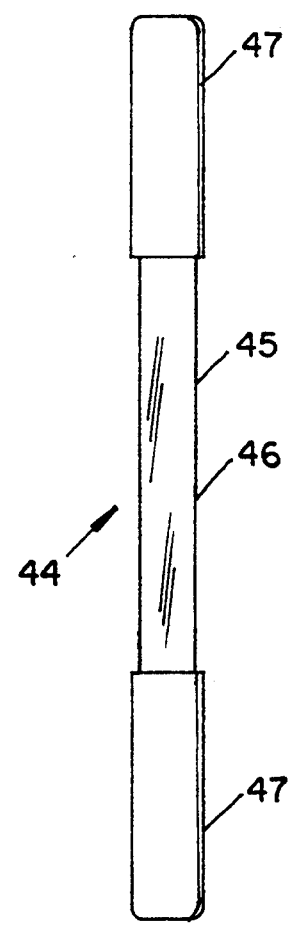
FIG. 11 is a front elevational view of the alternate embodiment shown in FIG. 10.
Figure 23:
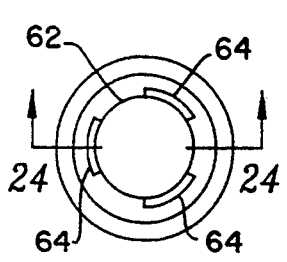
FIG. 23 is an enlargerd plan view of the biopsy punch and adapter of the alternate embodiment.
Figure 21:
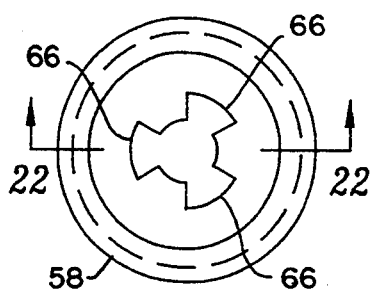
FIG. 21 is an enlarged plan view of the needle of the syringe.

Referring now to the drawings wherein like numerals designate like and corresponding parts throughout the several views, in FIGS. 1 through 4, inclusive, is illustrated, for purposes of describing our invention, a closure device for repair of resulting skin defect and controlling bleeding during a routine skin biopsy procedure with reduction of chances of inducing excessive scar tissue.

The closure device, generally designated by the numeral 20, is housed in a sterile container 21 and is comprised of a pre-cut circular sponge 22 and an applicator 23 for implanting the sponge 22 into a bleeding site caused by the excising of a specimen of skin for a biopsy. The applicator is comprised of a slender rod 24 and a fibrous cotton wad 25 attached to one end of the rod 24. The sterile sponge 22 is loosely attached to the other end of said rod 24. The sterile container 21 is comprised of a cylindrical body 26 and a detachable cap 27 at each end of the body 27.

The sterile sponge 22 is pre-cut to diameters which correspond to diameters of conventional skin punches (not shown) by way of example, 2, 3, 4, 5 and 6 millimeters. The sponge 22 is a water-insoluble, porous item which is absorbed completely, with little tissue reaction. When the sponge 22 is implanted into the bleeding site, the sponge 22 absorbs blood, swells and terminates the flow of blood in the bleeding site and by filling up the biopsy site defect promotes healing without the necessity of approximation of the defect sides by suturing.

The applicator rod 24 is preferably made from a plastic material. The end of the rod 24 to which the sponge is loosely attached is tapered to facilitate the mounting of the sponge 22. Adjacent to the taper 28 there is a circular flange 29 for locating the sponge 22 on the rod 24 and to assist in implanting the sponge 22 into the bleeding site.

One material which has been evaluated and found to be acceptable for practicing our invention is an absorbable gelatin sponge manufactured by the Upjohn Company under the registered trademark "GELFOAM". It is a water-insoluble, off-white, non-elastic, porous, pliable product made from purified pork skin gelatin USP granules and is available in the form of pads.

The method for using our invention consists of the following steps. The biopsy area is cleaned and draped to provide a sterile environment. The skin is next anesthetized by an intradermal injection of a suitable anesthesiology material. A proper size sterile punch is pressed against the skin and rotated to excise specimens of epidermis and subcutaneous tissue for biopsy.

The closure device 20 having a sponge 22 whose diameter corresponds to the diameter of the excised area is removed from the sterile container 21. The sponge 22 is positioned and implanted with the applicator 23 into the bleeding site. The applicator 23 is removed from the sponge 22, the applicator 23 is inverted and pressure is applied with fiber cotton wad 25 for approximately 30 to 60 seconds to seal the wound and stop bleeding. For this and other embodiments described herein, a topical antibiotic ointment such as Bacitracin or Bactoroban is applied to the biopsy site and a conventional sterile dressing (not shown) is applied over the ointment. The dressing is removed after approximately 24 hours. The wound site may need to be cleaned twice a day with rubbing alcohol or a hydrogen peroxide solution until healing has been completed.

With reference to FIGS. 5 through 9, inclusive, an alternate embodiment 33 is shown wherein a closely fitting circular sponge 34 is held in the interior of a biopsy punch 35. The sponge 34 is spaced a short distance from the cutting edge of a blade 36 to provide a space for the skin specimen to be excised by the punch 35. Above the sponge 34 there is a plunger 37 for implanting the sponge 34 into the wound after the sample has been excised. At the end of the punch 35 opposite the blade 36 there is a removable cap 38.

The punch 35 is comprised of a hollow cylindrical body 40 having a series of longitudinal serrations 40 for assisting in the rotation of the punch 35, the razor sharp circular blade 36 pressed into one end of the body 39 and removable cylindrical caps 41, 42 at each end of the body 39. One benefit of this embodiment is that the sponge 34 can be diametrically pre-compressed for improved retention when implanted into the bleeding site.

The sterile sponge 34 is implanted into the bleeding site in the following manner. After a specimen has been excised with the razor sharp blade 36, the cap 42 is removed to expose the end of the plunger 37. The specimen is removed from the punch 35 by depressing the plunger 37 and the sponge 34 is positioned over the bleeding site. The plunger 37 is further depressed to implant the sponge 34 into the bleeding site. After the sponge 34 has been implanted, pressure is applied to the sponge 34 by a conventional sterile cotton gauze (not shown) for approximately 30 to 60 seconds to terminate bleeding and seal the wound.

A third embodiment 44 of the invention is shown for purposes of illustrating the invention in FIGS. 10 through 13 inclusive. The third embodiment 44 is comprised of a sterile container 45 having a cylindrical body 46 and a pair of identical cylindrical caps 47 at each end of the body 46, a closely fitting cylindrical sponge 34 in the interior of the body 46 and a plunger 49. The body 46 is preferably made of a transparent plastic material such that the sponge 34 is visible. The plunger 49 is comprised of a slender cylindrical rod 50 and a cotton fiber wad 51 at one end of the rod 50.

The sterile sponge 34 is located close to the end of the body 46 whereby when the end caps 47 are removed from the body 46, the sponge 34 can be implanted into the bleeding site by depressing the plunger 49. With this embodiment 44 pressure can be applied to the sponge 34 with the cotton fiber wad 51 to seal the wound by further depressing the plunger 49 to expose the cotton fiber wad 51. With this embodiment 44 the sponge 34 may also be diametrically pre-compressed in the cylindrical body 46.

Figure 20:
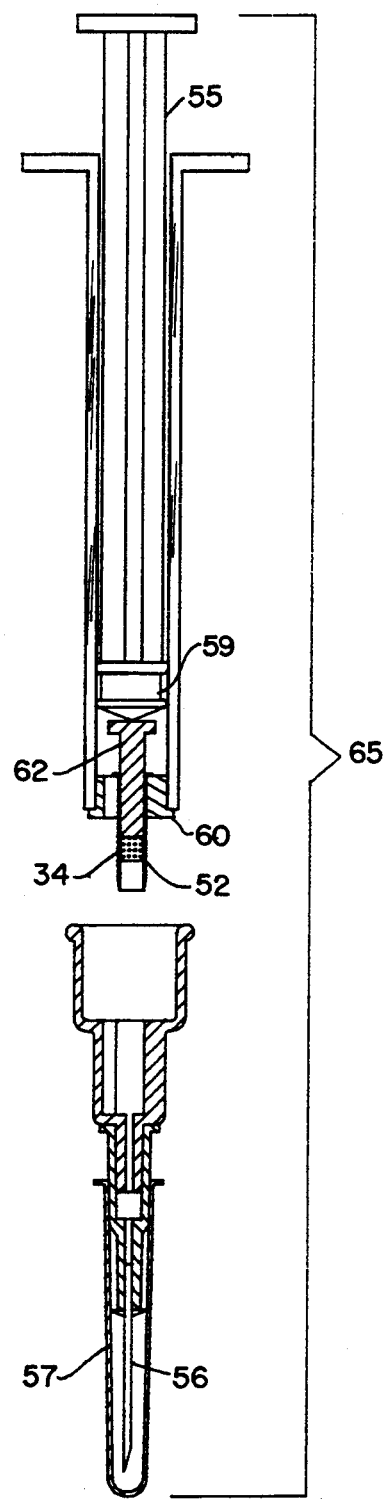
FIG. 20 is similar to FIG. 19 except showing the needle of the syringe and an adapter separated from the remainder of the closure device.

Referring now to FIGS. 14 through 26, inclusive, an alternate embodiment 65 is shown wherein a sterile sponge 34 is combined with a biopsy punch 52 and a syringe 53. The construction of the syringe 53 is generally depicted in FIGS. 19 and 20. The syringe 53 is comprised of a transparent body 54, a usual type plunger 55 which slidably engages body 54, a conventional needle 56, a detachable sterile cap 57, and an adapter 58 made from a rubber-like material. At the lower end of the plunger 55 there is the usual seal 59 made of a rubber like material.

As best seen in FIGS. 19 through 22, the needle 56 is lightly press-fitted into one end of the adapater 58. The other end of the adapter 58 is lightly press-fitted to the lower end of the syringe's body 54 such that the adapter 58 can be removed from the body 54 by hand to expose the biopsy punch 52 which is mounted to the lower end of the body 54 by means of a second adapter 60.

Referring now to FIGS. 23 through 26, the biopsy punch 52 is press fitted into an aperture 61 in the center of the adapter 60 which is mounted to the lower end of the syringe's body 54. Optional adapters are provided to accomodate variations in biopsy punch diameter. The sterile sponge 34 is pre-assembled into the interior of the punch 52 together with a cylindrical plunger 62. The upper end of the plunger 62 contacts the syringe's plunger 55 when the syringe's plunger 55 is in the fully engaged position. The upper end of the punch 52 has a narrow flange 63 which locates and assists in retaining the punch 52 in the adapter 60.

Figure 25:
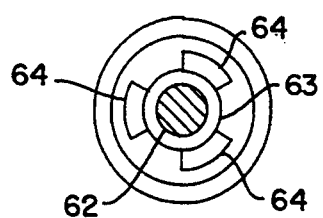
FIG. 25 is a cross-sectional view taken on the line 25—25 in FIG. 24.
Figure 24:
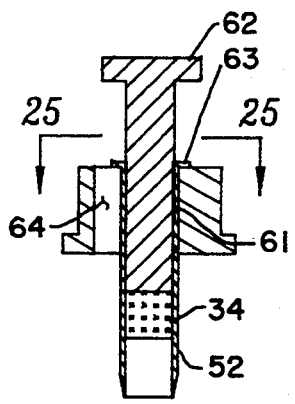
FIG. 24 is a cross-sectional view taken on the line 24—24 in FIG. 23.
Figure 26:
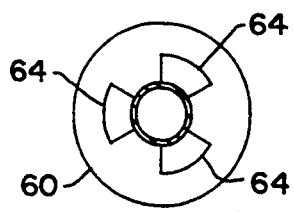
FIG. 26 is a bottom view of the biopsy punch and adapter.
Figure 22:
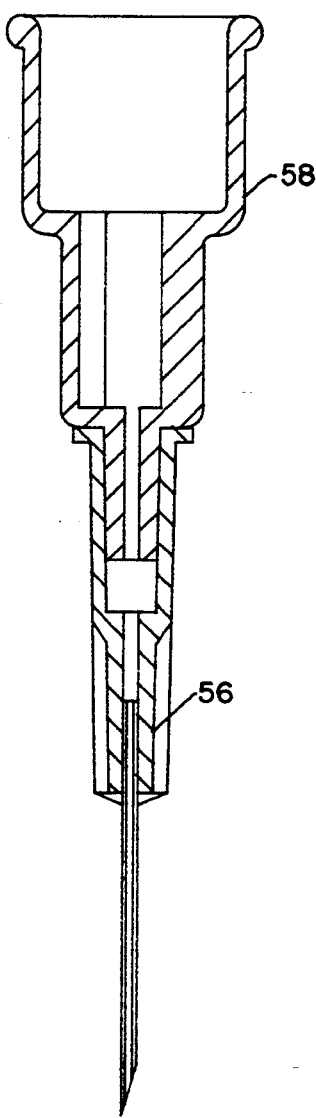
FIG. 22 is a cross-sectional view taken on the line 22—22 in FIG. 21.

As best seen in FIGS. 24 and 25, extending axially through the punch adapter 60 are three fluid passages 64 which are aligned with three axial fluid passages 66 in the needle adapter 58. The fluid passages 64 and 66 allow fluid to by-pass the sterile sponge 34 and plunger 62 when the device is used as a syringe 53.

The manner of using this embodiment during a routine biopsy is as follows. The syringe 53 is filled with an anesthetic (not shown) by removing the sterile cap 57, inserting the needle 56 into the anethesthic and withdrawing the plunger 55 from the body 54. During the withdrawal of the plunger 55, liquid anesthetic is drawn through the needle 56, through the axial passages 64 of the adapter 60 and into the body 54 of the syringe 53.

The skin of the biopsy site is then pierced by the pointed end of the needle 56 and the plunger 55 is depressed to anesthetize the biopsy site. The needle 56 is then withdrawn and removed from the body 54 by detaching the adapter 58 and needle 56 from the end of the syringe's body 54. After the needle 56 has been removed, the biopsy punch 52 is pressed against the skin and rotated to excise a cylinder shaped sample for the biopsy.

The syringe's plunger 55 is then partially depressed to extract the sample from the punch 52. Thereafter the punch 52 is positioned against the wound and the syringe's plunger 55 is further depressed to implant the sterile sponge 34 into the wound.

After the sponge 34 has been implanted, pressure is applied to the sponge 34 by a conventional sterile cotton gauze (not shown) for approximately 30 to 60 seconds to terminate bleeding and seal the wound.

From the foregoing it will be understood that our invention provides an improved closure device and method for performing a routine biopsy procedure. Moreover, it will be appreciated that our improved closure device provides numerous benefits, among which are, a reduction in cost and time, reduced handling of tissue, and a reduction in the likelihood of inducing the formation of excessive scar tissue.

Although but several embodiments of our invention have been illustrated and described, it is not our intention to limit our invention to these embodiments since other embodiments can be provided by substitutions in materials and modifications in the shape, number and arrangements of parts and steps in our closure device and changes in steps in our method without departing from the spirit thereof.

We claim:

1. A closure device for the repair of skin tissue, controlling bleeding, and reducing the likelihood of inducing excess scar tissue during a routine skin biopsy procedure, comprising: a biopsy punch having a thin sharp circular blade for excising a cylindrical specimen of epidermis and subcutaneous tissue during a routine skin biopsy procedure; a a thin pre-formed cylindrical sponge stored inside of said punch of about the same size and shape as said excised specimen of epidermis and subcutaneous tissue, said sponge made from a foam material which swells and is absorbed in a biopsy site from which said specimen has been excised with little tissue reaction, said sponge being pre-formed to a diameter which is approximately equal to the diameter of said circular blade of said punch used for taking said specimen of skin for a biopsy from said biopsy site; and an applicator for implanting said sterile sponge into said biopsy site after the excising of said specimen by said punch; and a means for applying pressure to said sponge for a short interval of time after said sponge has been implanted into said biopsy site.

2. The closure device recited in claim 1 wherein the diameter of said pre-formed cylindrical sponge is equal to the diameter of said circular blade of said punch.

3. The closure device recited in claim 1 wherein the diameter of said pre-formed cylindrical sponge is greater than the diameter of said circular blade of said punch.

4. The closure device recited in claim 1 wherein said sponge is a water-insoluble, non-elastic, porous and pliable product made from purified pork skin gelatin USP granules.

5. A closure device for the repair of skin tissue, controlling bleeding, and reducing the likelihood of inducing excess scar tissue, during a routine skin biopsy procedure, comprising: a thin cylindrical surgical punch having a hollow body; a razor sharp circular blade attached to one end of said hollow body, said punch having a sharp cutting edge at one end of said punch for excising a specimen of of epidermis and subcutaneous skin for a biopsy; a thin closely fitting cylindrical sponge of about the same size and shape as said excised specimen stored in the interior of said punch a short distance from said sharp cutting edge of said punch, said cylindrical punch having a diameter which is about the same as the diameter of said sharp cutting edge of said punch; an applicator, stored in the interior of said hollow body for implanting said sponge into a bleeding site caused by the excising of said specimen, said applicator having one portion adjacent to said cylindrical sponge and an opposite end portion extending out of said body for implanting said sponge into said bleeding site after the excising of said specimen.

6. The closure device recited in claim 5, further comprising a cylindrical cap removably attached to each end portion of said hollow body for enclosing said applicator and said cylindrical sponge.

7. The closure recited in claim 5 wherein said sponge is diametrically pre-compressed when said sponge is in said interior of said body.

8. A method for performing a skin biopsy procedure, said method comprising the steps of: pressing and rotating a proper size surgical punch against the skin to excise a specimen of epidermis and subcutaneous tissue; implanting a pre-formed closely fitting sterile sponge of about the same size and shape as said excised specimen, stored in the interior of said punch into the space from which said specimen was excised; applying pressure to said sterile sponge to control bleeding from said excised area.

9. The method recited in claim 8 wherein said pressure is applied to said sponge for 30 to 60 seconds.

10. The method recited in claim 8 further comprising the step of cleaning and draping said biopsy area before the excising of said specimen.

11. The method recited in claim 10 further comprising the step of anesthetizing the biopsy area by an intradermal injection of a suitable anesthesiology material after said biopsy area has been cleaned and draped.

12. The method recited in claim 8 further comprising the step of applying a topical antibiotic ointment to said sponge and the area surrounding said sponge after said bleeding has been controlled.

13. The method recited in claim 12 further comprising the step of applying a dressing over said excised area after said topical ointment has been applied.

14. The method recited in claim 13 further comprising the steps of removing said dressing and cleaning said excised area twice a day with rubbing alcohol or a hydrogen peroxide solution until healing has been completed.

* * * * *